US 7,776,044 B2

(12) United States Patent  
Pendleton et al.

(10) Patent No.: US 7,776,044 B2  
(45) Date of Patent: Aug. 17, 2010

(54) TIBIAL TRAY INSERTER

(75) Inventors: John E. Pendleton, Fort Wayne, IN (US); Jeff C. Blaylock, Fort Wayne, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 727 days.

(21) Appl. No.: 11/018,565

(22) Filed: Dec. 21, 2004

(65) Prior Publication Data

US 2006/0136067 A1 Jun. 22, 2006

(51) Int. Cl.  
*A61B 17/36* (2006.01)
(52) U.S. Cl. ........................................ 606/88
(58) Field of Classification Search ......... 606/53–105.5  
See application file for complete search history.

(56) References Cited

U.S. PATENT DOCUMENTS

| 4,459,985 | A | * | 7/1984 | McKay et al. | 606/100 |
| 4,633,862 | A | * | 1/1987 | Petersen | 606/88 |
| 4,706,660 | A | * | 11/1987 | Petersen | 606/86 |
| 5,002,547 | A | * | 3/1991 | Poggie et al. | 606/88 |
| 5,035,700 | A | * | 7/1991 | Kenna | 606/88 |
| 5,037,423 | A | * | 8/1991 | Kenna | 606/88 |
| 5,122,144 | A | * | 6/1992 | Bert et al. | 606/88 |
| 5,129,908 | A | * | 7/1992 | Petersen | 606/88 |
| 5,275,603 | A | * | 1/1994 | Ferrante et al. | 606/86 |
| 5,578,039 | A | * | 11/1996 | Vendrely et al. | 606/88 |
| 5,690,636 | A | * | 11/1997 | Wildgoose et al. | 606/88 |
| 5,702,463 | A | * | 12/1997 | Pothier et al. | 623/20.32 |
| 6,610,065 | B1 | * | 8/2003 | Branch et al. | 606/84 |
| 6,786,931 | B2 | * | 9/2004 | Hazebrouck | 623/22.42 |
| 2004/0073315 | A1 | * | 4/2004 | Justin et al. | 623/20.15 |
| 2004/0093083 | A1 | * | 5/2004 | Branch et al. | 623/17.11 |
| 2004/0249467 | A1 | * | 12/2004 | Meyers et al. | 623/20.24 |
| 2006/0095043 | A1 | * | 5/2006 | Martz et al. | 606/90 |
| 2006/0184198 | A1 | * | 8/2006 | Bales et al. | 606/205 |

OTHER PUBLICATIONS

Photographs of Gripping Tibial Tray Impactor, Zimmer, Inc., Dec. 12, 2000.  
Photographs of Gripping Tibial Tray Impactor, Zimmer, Inc., Apr. 9, 2003.  
NexGen® Complete Knee Solution, Micro-Mill® Instrumentation Surgical Technique, 97-5970-103, Zimmer, Inc. 1998.

* cited by examiner

*Primary Examiner*—David Isabella  
*Assistant Examiner*—Ann Schillinger  
(74) *Attorney, Agent, or Firm*—Baker & Daniels LLP

(57) ABSTRACT

A tibial tray inserter for use during knee joint replacement surgery is provided.

4 Claims, 5 Drawing Sheets

TIBIAL TRAY INSERTER

FIELD OF THE INVENTION

The invention relates to instrumentation for performing an orthopaedic surgical procedure. More particularly, the invention relates to a tibial tray inserter for use with a tibial tray implant during knee joint replacement surgery.

BACKGROUND

Degenerative and traumatic damage to the articular cartilage of the knee joint can result in pain and restricted motion. Prosthetic joint replacement is frequently utilized to alleviate the pain and restore joint function. In this procedure, the damaged compartments of the joint are cut away and replaced with prosthetic components. Typically a "C"-shaped femoral component is mated with the cut end of the femur and a tibial component is mated with the cut end of the tibia.

The use of modular components, especially modular tibial components, has become popular because it allows the surgeon to assemble components in a variety of configurations at the time of surgery to meet specific patient needs relative to size and geometry. For example, modular tibial components may include separate tray and bearing components that can be assembled in a variety of configurations of bone coverage area, bearing thickness, kinematic constraint, and bone attachment mechanism. For example, the tray may be provided in a variety of styles including cemented, bone ingrowth, flat, finned, and stemmed.

During a knee joint replacement surgical operation, it is necessary to manipulate the implant components into position within the joint and/or hold them in position while subsequent operations are carried out such as joining fasteners. Manipulating these components can be difficult due to small gripping areas on the components, the depth and/or narrowness of the surgical wound, and/or the need to impart relatively large gripping and/or positioning forces. In particular, minimally invasive surgical procedures require manipulating components through small incisions.

SUMMARY

The present invention provides a tibial tray inserter for use during knee joint replacement surgery.

In one aspect of the invention, a tibial tray inserter for gripping a tibial tray component of a knee joint implant includes a handle, a plunger mounted on the handle for translation relative to the handle, and an actuator. The handle includes a shoulder engageable with a peripheral rail of the tray in force transmitting relationship. The plunger includes a first dovetail groove engageable with a tibial tray dovetail. The plunger is translatable between a first position in which the plunger and shoulder grip the tibial tray and a second position in which the plunger and shoulder release the tibial tray. The actuator is actuable to move the plunger between the first and second positions.

In another aspect of the invention, a combination includes a tibial tray component of a knee joint implant and an inserter for inserting the tray component into a surgical site between a tibia and a femur. The inserter has a handle and a head attached to the handle. The head is engageable with the tibial tray component to grip the tibial tray component. The inserter head has a thickness parallel to the longitudinal axis of the tibia sized to permit the tibial tray and inserter to be inserted together into the gap between the tibia and femur while the inserter is gripping the tray.

In another aspect of the invention, a method of manipulating a tibial tray component of a knee joint implant comprises the steps of providing an instrument having a handle, the handle including a shoulder engageable with the peripheral rail of the tray surface in force transmitting relationship; a plunger mounted on the handle for translation relative to the handle, the plunger including a first dovetail groove engageable with the tray dovetail, the plunger being translatable between a first position in which the plunger and shoulder grip the tibial tray and a second position in which the plunger and shoulder release the tibial tray; and an actuator mounted to the handle and actuable to move the plunger between the first and second positions; gripping the tibial tray component with the inserter; and positioning the tibial tray component at a desired location with the inserter.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Embodiments of a tibial tray inserter include a handle and a plunger mounted for movement relative to the handle. The handle is engageable with a first portion of the tibial tray in a first force transmitting direction and the plunger is engageable with a second portion of the tibial tray in a second force transmitting direction. By engaging the handle with the first portion of the tibial tray and engaging the plunger with the second portion of the tibial tray, opposing forces are generated that grip the tibial tray. For example, where the tibial tray includes a peripheral rail and a dovetail boss for retaining a polymer bearing component, the handle may include a shoulder for engaging the rail and the plunger may include a dovetail slot for engaging the dovetail boss. With the handle engaging the rail, the plunger may be driven into tight gripping engagement with the dovetail boss.

Figure 1:
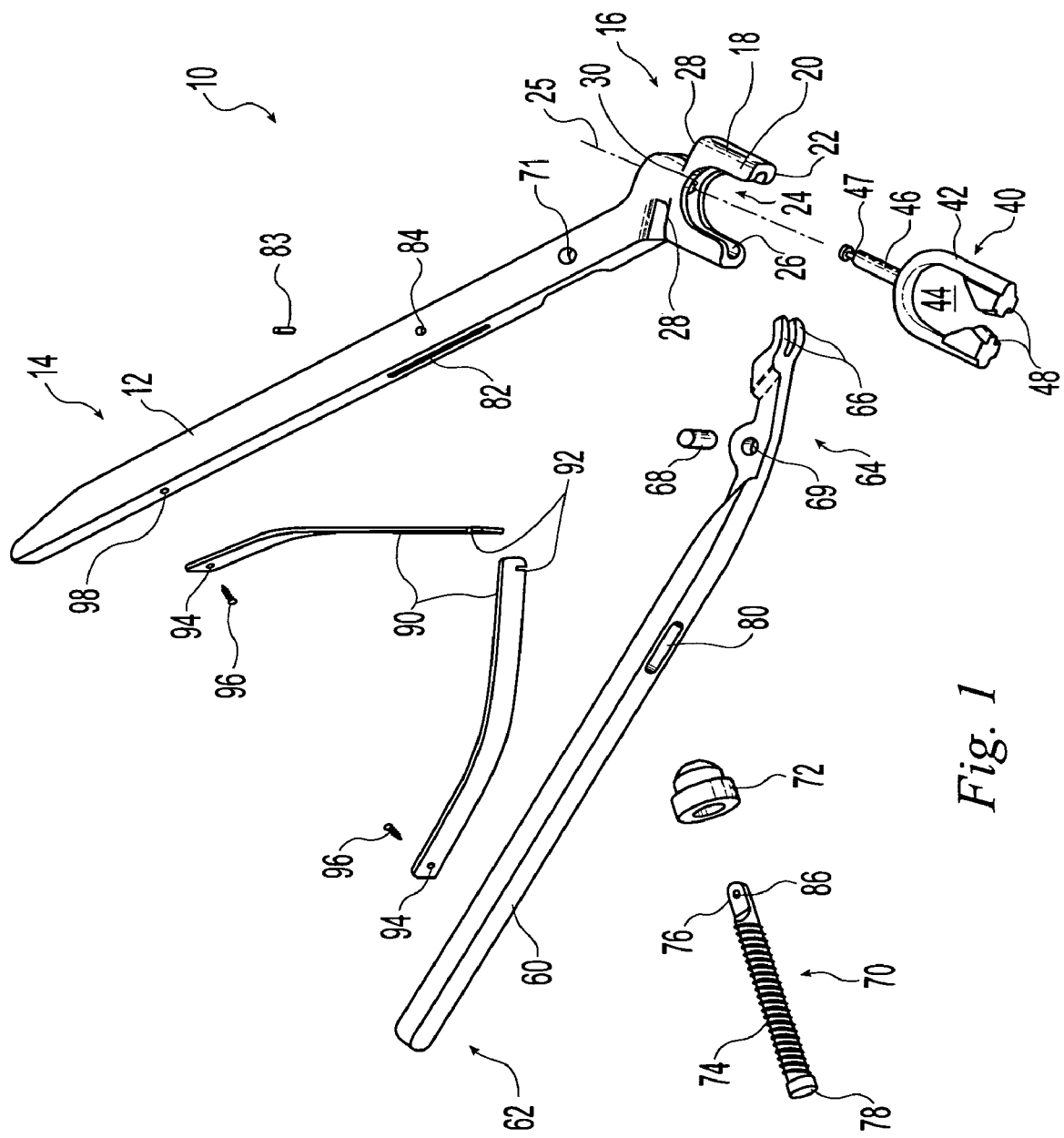
FIG. 1 is an exploded perspective view of a tibial tray inserter according to the present invention.
Figure 2:
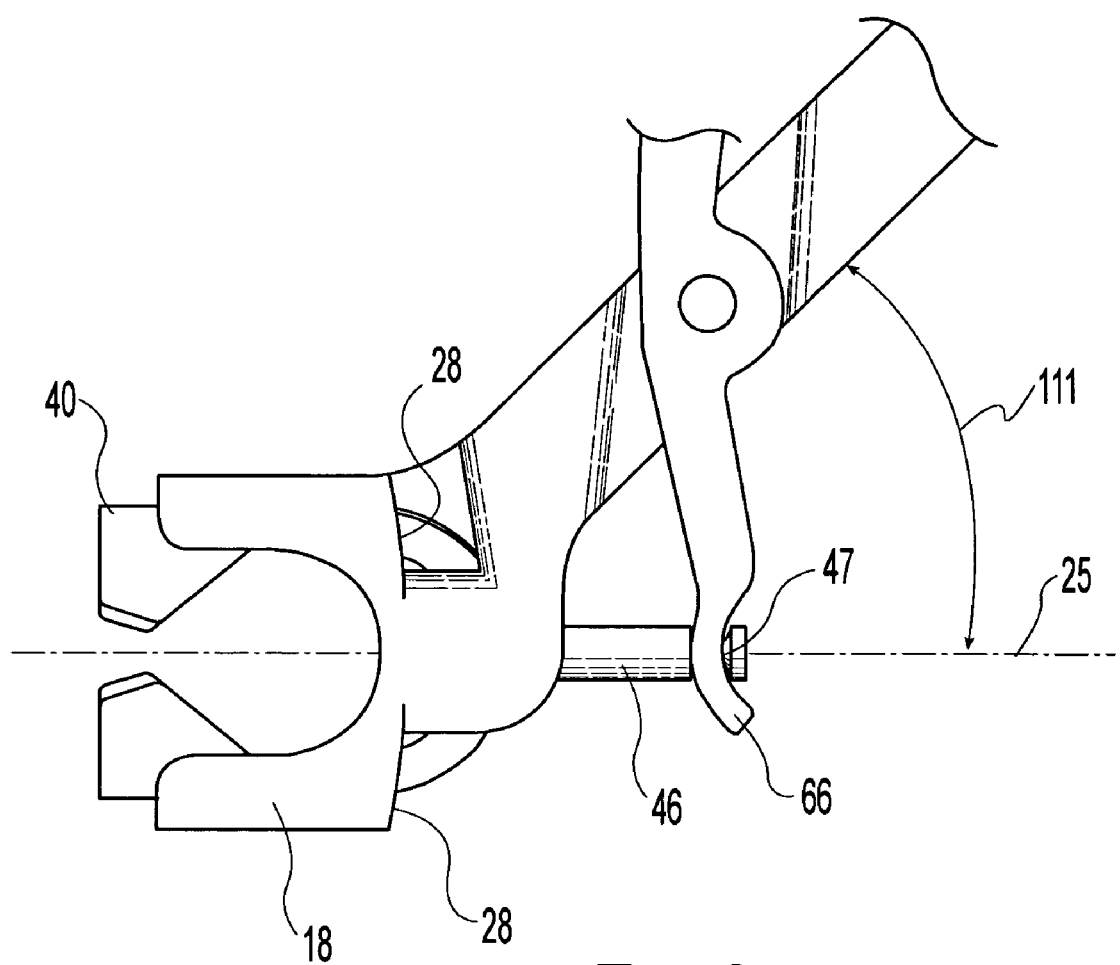
FIG. 2 is a top plan detail view of the gripping end of the tibial tray inserter of FIG. 1.
Figure 3:
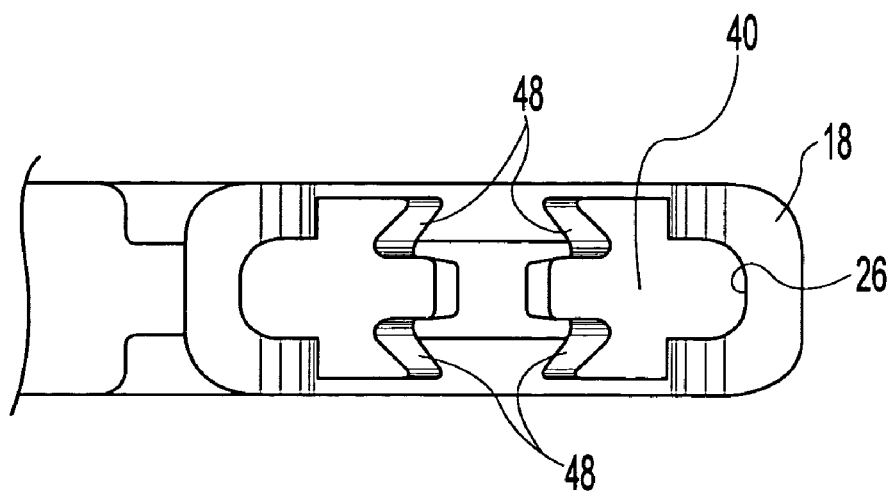
FIG. 3 is a side elevation detail view of the gripping end of the tibial tray inserter of FIG. 1.
Figure 4:
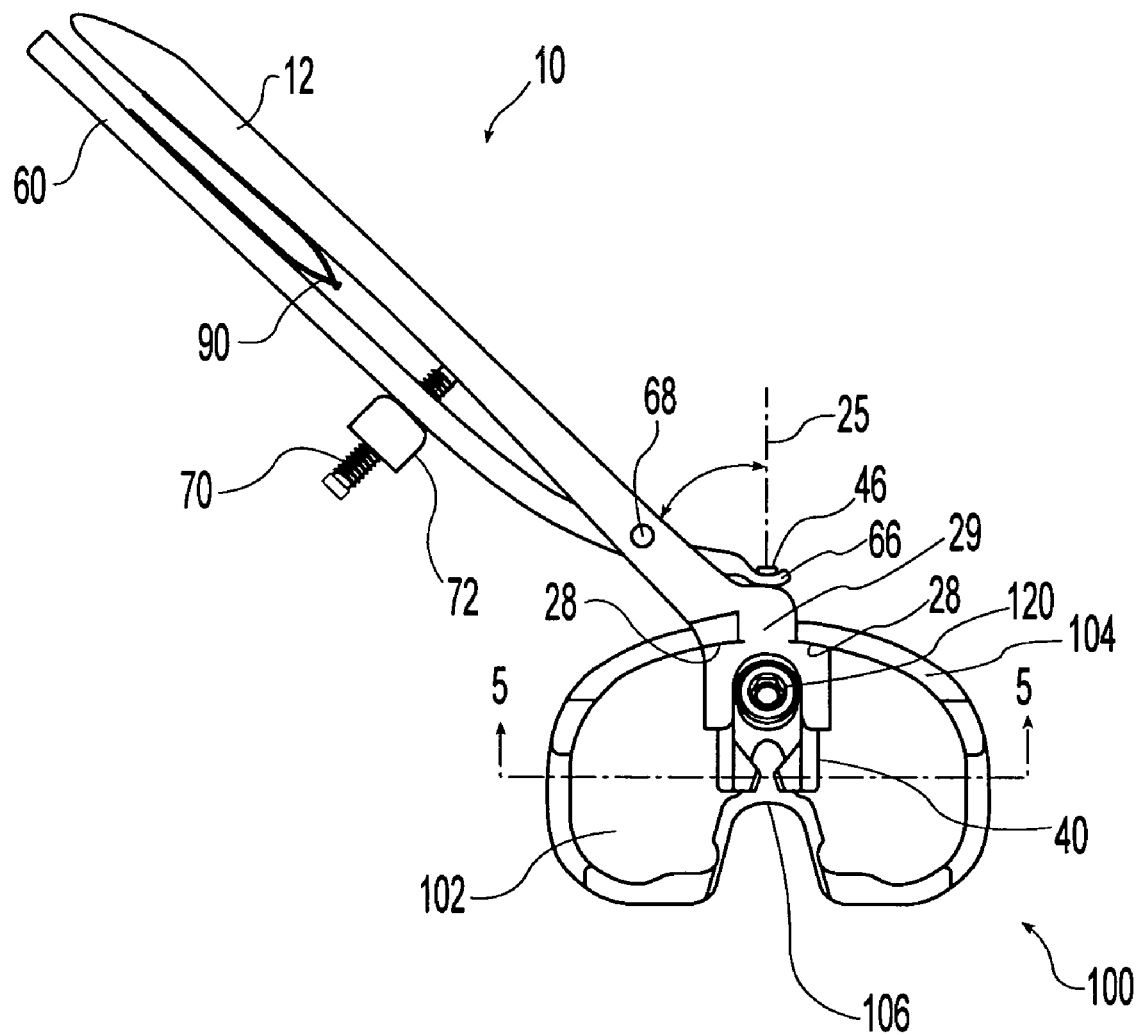
FIG. 4 is a top plan view of the tibial tray inserter of FIG. 1 engaged with a tibial tray.
Figure 5:
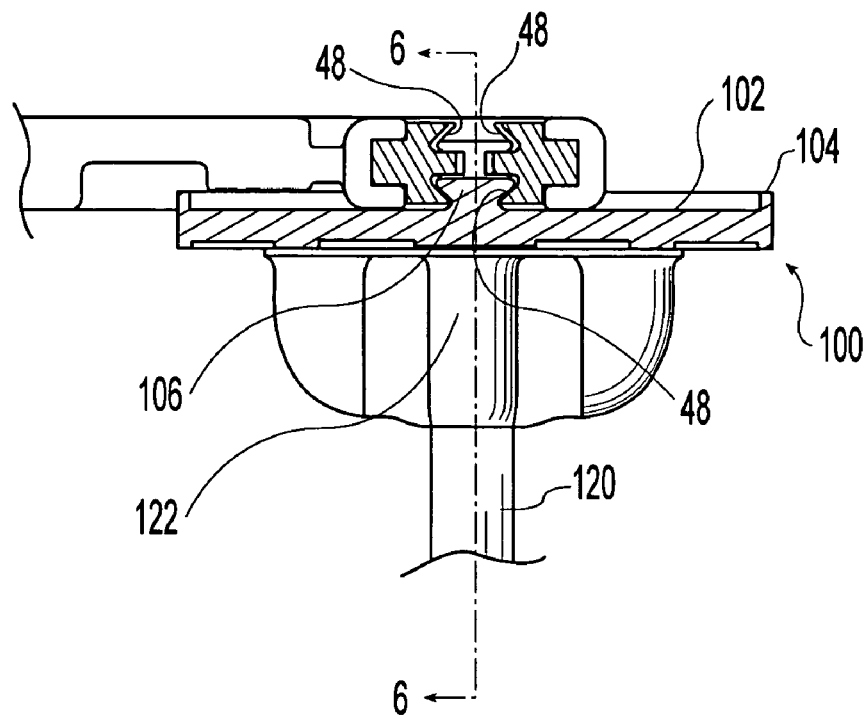
FIG. 5 is a sectional view taken along line 5-5 of FIG. 4.
Figure 6:
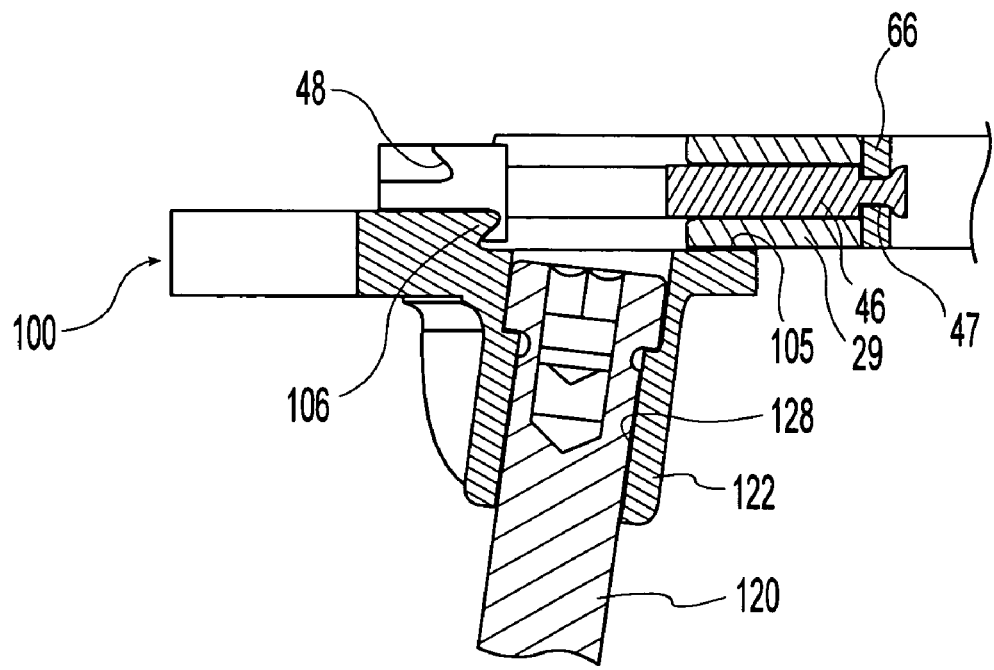
FIG. 6 is a sectional view taken along line 6-6 of FIG. 5.

FIGS. 1-3 depict an illustrative embodiment of a tibial tray inserter 10 according to the present invention. The inserter includes a handle 12 having a distal gripping end 14 and a proximal working end 16. The working end 16 includes a generally planar rectangular head 18 having first and second planar sides 20, 22. A "U"-shaped opening 24 is formed through the head 18 from the first side 20 to the second side 22 and is open proximally. The "U"-shaped opening 24 is symmetric about an axis 25 extending from its proximal opening distally through the head 18. A "U"-shaped slot 26 is formed in the head 18 surrounding the "U"-shaped opening 24. The head 18 includes a shoulder 28 on the distal side of the head, opposite the "U"-shaped opening 24. The shoulder 28 is formed by selectively thinning the handle 12 adjacent to the head 18. In the illustrative inserter 10, the shoulder 28 is interrupted in the middle by a central portion 29 of the head 18. A through bore 30 communicates from the "U"-shaped slot 26 distally through the head 18 along the axis 25.

A plunger 40 includes a "U"-shaped body 42 mounted within the "U"-shaped slot 26 for translation along the axis 25. The "U"-shaped body 42 includes an opening 44 such that with the body 42 mounted in the slot 26, there is an open passage through the head 18 and plunger 40. A shaft 46 extends distally from the body 42 and is sized to slide through the through bore 30 in the head 18 and extend distally from the head 18. The shaft includes an annular groove 47 adjacent to its distal end. The plunger 40 includes a dovetail groove 48 formed at the proximal end of the plunger 40. As best seen in FIG. 3, the illustrative example includes two grooves 48 to permit the inserter 10 to be used from both medial and lateral directions on both left and right knees. The plunger 40 is translatable in the slot 26 between a first position in which the plunger 40 is relatively closer to the shoulder 28 and a second position in which the plunger 40 is relatively further from the shoulder 28.

An actuator 60 is mounted to the handle 12 in order to provide mechanical advantage in translating the plunger 40. The actuator 60 includes a distal gripping end 62 and a proximal working end 64. The working end 64 includes a pair of tines 66 engageable with the annular groove 47 of the plunger shaft 46. The actuator 60 is joined to the handle 12 for relative pivoting motion by a pivot pin 68 fit into holes 69, 71 in the actuator 60 and handle 12. The pivot pin 68 is positioned relatively nearer the working ends 64, 16 of the actuator 60 and handle 12 to create a mechanical advantage at the working ends 64, 16. Moving the gripping ends 62, 14 of the actuator and the handle toward one another from an open position to a closed position causes the tines 66 to drive the shaft 46 proximally through bore 30 and thereby move the plunger 40 proximally from the first position in which the plunger 40 is relatively closer to the shoulder 28 to the second position in which the plunger 40 is extended from the head 18 and relatively further from the shoulder 28.

A locking mechanism is provided to lock the actuator 60 and handle 12 in the closed position. The locking mechanism includes a locking screw 70 and a locking nut 72. The locking screw 70 includes a threaded shaft 74 having a first end with a flattened mounting tang 76 and a second end with an enlarged head 78. The locking screw 70 slides through a slot 80 in the actuator 60 and the tang 76 fits into a slot 82 in the handle 12. A pin 83 is pressed into a hole 84 in the handle 12 and a hole 86 in the tang 76 to connect the locking screw 70 to the handle 12 while allowing the locking screw 70 to pivot about the pin 83. The actuator 60 and handle 12 may be locked in the closed position by advancing the locking nut 72 along the locking screw 70 until it abuts the actuator 60. The enlarged head 78 prevents the locking nut 72 from being unscrewed from the locking screw 70 over the second end.

A pair of leaf springs 90 is mounted between the actuator 60 and handle 12 to bias them away from one another toward the open position. Each spring 90 includes a notch 92 at a first end to allow them to interleave. Each spring 90 includes a hole 94 at a second end to receive a screw 96 that threads into a hole 98 in the handle 12 and the actuator 60 to attach the springs 90 to the handle 12 and the actuator 60.

FIGS. 4-7 depict the inserter 10 in use with a tibial tray implant 100. The tibial tray 100 includes a generally planar tray surface 102 and a peripheral rail 104 extending around at least a portion of the tray perimeter and projecting above the tray surface 102. The tibial tray 100 further includes a dovetail boss 106 projecting above the tray surface 102. In the illustrative example, the rail 104 and dovetail boss 106 are configured to retain a polymer bearing component (not shown) on the tibial tray 100. The inserter 10 is configured to also engage the rail 104 and dovetail boss 106 to grip the tibial tray 100 during insertion. In use, the inserter 10 is positioned over the surface 102 of the tibial tray with the dovetail groove 48 of the plunger facing the dovetail boss 106. The shoulder 28 is engaged with the rail 104. In the illustrative example, the central portion 29 of the head 18 fits into a notch 105 in the rail 104 and the shoulder 28 engages the rail on each side of the central portion 29. The actuator 60 is pressed toward the handle 12 toward the closed position to extend the plunger 40 into engagement with the dovetail boss 106. With the actuator 60 and handle 12 maintained in the closed position, the locking nut 72 is advanced until it abuts the actuator 60 to lock it in the closed position. The pivot pin 68 is positioned so that the force pressing the actuator 60 and handle 12 together is magnified at the plunger 40 to press the plunger 40 firmly against the dovetail boss 106 and the shoulder 28 firmly against the rail 104. The opening 44 in the plunger 40 allows access to the surface 102 of the tibial tray 100 while the inserter 10 is gripping the tray 100. While particular male/female interlocking features have been illustrated to connect the inserter 10 and tray 100, engagement mechanisms other than dovetails are contemplated. Furthermore, reversal of the gender of the engagement mechanism components between the inserter 10 and tray 100 is also contemplated and within the scope of the present invention.

Figure 7:
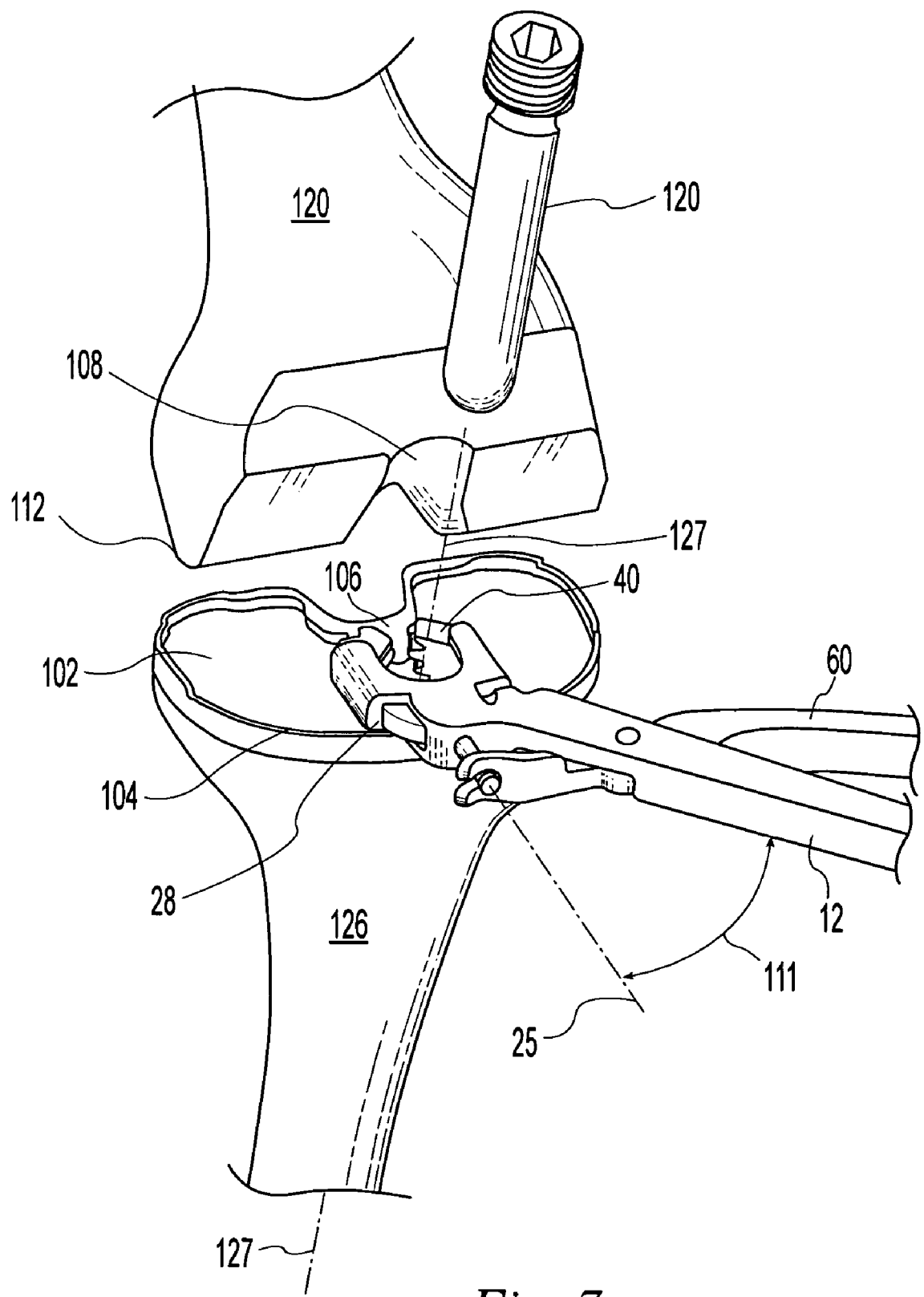
FIG. 7 is a perspective view of the tibial tray inserter of FIG. 1 shown in use to insert a tibial tray.

The inserter 10 facilitates minimally invasive surgical procedures in which the knee replacement is done through small incisions. The generally flat, low profile layout of the head 18 results in a low profile grip on the tibial tray 100 and allows the head 18 and tray 100 to fit through narrow spaces. For example, as seen in FIG. 7, flexion and extension gaps are created between the femur 120 and tibia 126 when they are cut to accommodate implants during knee replacement surgery. These gaps are typically approximately 20 mm. The inserter head 18 thickness in the vertical direction parallel to the longitudinal axis 127 of the tibia 126 is sized so that the inserter 10 and tray 100 will fit within the flexion and extension gaps with the inserter 10 locked onto the tray 100. For example, for a 5 mm thick tray, the head thickness is preferably less than 15 mm. The illustrative inserter 10 has a head thickness of approximately 7.6 mm.

In addition, the head 18 locks onto the tray 100 in the center of the tray 100 so that it is inserted under the intercondylar notch 108 of the femur 110 and avoids impingement with the posterior femoral condyles 112. Furthermore, the handle 12 and actuator 60 are angularly offset 111 from the axis 25 to facilitate a side approach to the knee. The offset 111 also provides clearance so that the handle 12 and actuator 60 do not impinge the patellar tendon (not shown) which runs down the center of the knee joint. Preferably the offset 111 is between 0 and 110 degrees. More preferably, the offset 111 is between 30 and 90 degrees. Still more preferably, the offset 111 is between 30 and 60 degrees. In the illustrative inserter 10, the offset 111 is approximately 45 degrees.

In the illustrative example, a stem extension 120 is provided with the tibial tray 100 to extend the tibial stem 122 further into the tibia 126 to enhance the stability of the tray 100 on the tibia 126. In a minimally invasive surgical procedure, the stem extension 120 is dropped down through the planar surface 102 of the tibial tray 100 into an axial bore 128 in the stem 122 after the tray 100 is positioned on the tibia 126. The stem extension 120 is inserted after the tray 100 is inserted into the joint because the incision required to insert the components separately is smaller than the incision required to insert the components if they were preassembled. The central opening through the head 18 and plunger 40 assembly resulting from the alignment of the "U"-shaped opening 24 in the head with the opening 44 in the plunger 40 is positioned to align with the axial bore 128 through the stem 122 so that the stem extension 120 may be inserted while the inserter 10 is gripping the tray 100. The stem extension 120 is then screwed into the tray 100 and a torque wrench is used to apply a 95 in-lb tightening torque. The inserter 10 provides a grip to countertorque the tray 100 while the stem extension 120 is tightened and to hold the tray 100 stationary so that the tray 100 does not move out of position or disturb bone cement positioned between the tray 100 and tibia 126. A secure grip is provided by the engagement of the inserter 10 with the dovetail boss 106 and rail 104 to support the application of large counter torque forces to the tray 100.

Although illustrative embodiments of a tibial tray inserter and its use have been described and illustrated in detail, it is to be understood that the same is intended by way of illustration and example only and is not to be taken by way of limitation. Accordingly, variations in and modifications to the instrument and its use will be apparent to those of ordinary skill in the art, and the following claims are intended to cover all such modifications and equivalents.

What is claimed is:

1. In combination, a tibial tray component of a knee joint implant and an inserter for inserting the tray component into a surgical site between a tibia and a femur, the tibia and femur being prepared to receive the knee joint implant by cutting away portions of the bones to form a gap between the bones of a predetermined width, the tibia having a longitudinal axis, the combination comprising:

a tibial tray component having a tray thickness parallel to the longitudinal axis of the tibia, a tray surface, a peripheral rail extending from the tray surface, and a dovetail boss, and an inserter having a plunger, a handle, and a head attached to the handle, the head having a shoulder, the shoulder of the head being engageable with the peripheral rail of the tibial tray component and the plunger being engageable with the dovetail boss of the tibial tray component to grip the tibial tray component, whereby, with the head and the plunger cooperating to grip the tibial tray component, linear movement of the inserter in any direction results in corresponding linear movement of the tray component, the head of the inserter having a thickness parallel to the longitudinal axis of the tibia sized to permit the tibial tray and inserter to be inserted together into the gap between the tibia and femur while the inserter is gripping the tray.

2. The combination of claim 1 wherein the tibial tray includes a through bore generally corresponding to the longitudinal axis of the tibia, the combination further comprising a stem extension insertable through the through bore to extend through the tibial tray and into the tibia along the longitudinal axis of the tibia.

3. The combination of claim 2 wherein the inserter includes an opening in the head to permit passage of the stem extension through the head and into the through bore of the tibial tray while the inserter is gripping the tray.

4. The combination of claim 2 wherein the inserter grips the tray in torque transmitting relationship.

* * * * *